(12) United States Patent
Dobbs et al.

(10) Patent No.: US 7,009,170 B2
(45) Date of Patent: Mar. 7, 2006

(54) ACTIVE REMOTE SENSING USING A SIMULTANEOUS SPECTRAL SAMPLING TECHNIQUE

(75) Inventors: Michael E. Dobbs, Fort Wayne, IN (US); Jeff D. Pruitt, Fort Wayne, IN (US); Matthew L. Gypson, Fort Wayne, IN (US); Benjamin R. Neff, Fort Wayne, IN (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 334 days.

(21) Appl. No.: 10/603,695

(22) Filed: Jun. 26, 2003

(65) Prior Publication Data
US 2004/0263851 A1    Dec. 30, 2004

(51) Int. Cl.
*H01J 40/14* (2006.01)
*H01J 5/16* (2006.01)
(52) U.S. Cl. .................. 250/226; 250/214 A; 250/574
(58) Field of Classification Search ............ 250/214 A, 250/573–575, 226; 327/514; 356/73.1, 356/340
See application file for complete search history.

(56) References Cited

U.S. PATENT DOCUMENTS

| | | | |
|---|---|---|---|
| 3,676,005 A | 7/1972 | Chance | |
| 5,339,155 A | 8/1994 | Partridge et al. | |
| 5,550,636 A | 8/1996 | Hagans et al. | |
| 6,064,488 A * | 5/2000 | Brand et al. | 356/440 |
| 6,473,181 B1 | 10/2002 | Oakberg | |
| 6,594,003 B1 * | 7/2003 | Horiuchi et al. | 356/73.1 |
| 2004/0212804 A1 * | 10/2004 | Neff et al. | 356/435 |

OTHER PUBLICATIONS

K. Namjou et al.: "Sensitive absorption spectroscopy with a room-temperature distributed-feedback quantum-cascade laser," Feb. 1, 1998, vol. 23, No. 3, OPTIC LETTERS, pp. 219-221.
"Alpes Lasers: Applications," http://www.alpeslasers.ch/application/Application.htm, 4 pages.
Co-pending U.S. Appl. No. 10/419,797 entitled, "Active Remote Sensing Using Spectral Lock-In Technique," filed Apr. 22, 2003, 26 page specification, 6 sheets of drawings.
"Application Note 7, FM Spectroscopy With Tunable Diode Lasers," New Focus, San Jose, California, 2001, pp. 1-10.
European Search Report of Applications No. 08250489EP dated Oct. 25, 2004.

(Continued)

*Primary Examiner*—David Porta
*Assistant Examiner*—Patrick J. Lee
(74) *Attorney, Agent, or Firm*—RatnerPrestia

(57) ABSTRACT

A system for sensing a characteristic of a sample may include a tunable source configured to emit optical radiation that varies over a wavelength range at a sweep frequency and a reference source configured to emit optical radiation at a reference wavelength. A first modulator may be configured to modulate the first optical radiation at a first frequency, and a second modulator may be configured to modulate the second optical radiation at a second frequency that is different from the first frequency and the sweep frequency. A science detector may be configured to detect the optical radiation from the first modulator and the second modulator after interaction with the sample and generate a science signal. A number of lock-in amplifiers may be respectively configured to generate components of the science signal that are present at the first and second frequencies. A processor may be configured to determine a characteristic of the sample based on the components of the science signal that are present at the first and second frequencies.

22 Claims, 8 Drawing Sheets

OTHER PUBLICATIONS

Michael Dobbs "Validation of Design for Space Based Tunable Diode Laser Absorption Spectroscopy Payload", Proceedings of the SPIE—The International Society for Optical Engineering SPIE-Int. Soc. Opt. Eng. USA, vol. 4817, Jul. 10, 2002, pp. 123-128.

International Search Report and the Written Opinion of the International Searching Authority of Application No. PCT/US2004/012379 dated Aug. 30, 2004.

I. Dubinsky et al., "Frequency-Modulation-Enhanced Remote Sensing", Applied Physics B (Lasers and Optics), Oct. 1998, Springer-Verlag, Germany, vol. B67, No. 4, Oct. 1, 1998, pp. 481-492.

Liang-guo Wang "A H/sub 2/0(v) Sensor System for Combustion Diagnostics Using Both Direct Absorption and Frequency Modulation Spectroscopy", 1995, New York, NY, USA, IEEE, USA, Oct. 30, 1995, pp. 329-333 vol. 2.

Daniel B. Oh et al., "Frequency Modulation Multiplexing for Simultaneous Detection of Multiple Gases by Use of Wavelength Modulation Spectroscopy with Diode Laswers", Applied Optics, Apr. 20, 1998, Optical Sociey of America, USA, vol. 37, No. 12, Apr. 20, 1998, pp. 2499-2501.

A. M. Bullock et al, "Measurement of Absorption Line Wing Structure by Wavelength Modulation Spectroscopy" Applied Physics Letters, American Institute of Physics., New York, US, vol. 70, No. 10, Mar. 10, 1997, pp. 1195-1197.

\* cited by examiner

ACTIVE REMOTE SENSING USING A SIMULTANEOUS SPECTRAL SAMPLING TECHNIQUE

BACKGROUND OF THE INVENTION

1. Field of the Invention

This invention relates to remote sensing and, more particularly, to active remote sensing.

2. Description of Related Art

Active remote sensing may be conceptualized as viewing radiation reflected and/or emitted from a certain location in one or more wavelength regions. Active remote sensing typically utilizes one or more sources of radiation (e.g., infrared, visible, or ultraviolet light) to illuminate a target area while measuring the reflected, scattered and/or emitted radiation at one or more detectors. Such remote sensing may be performed from a moving platform or from a stationary location, each of which may be spatially remote from the target area.

One scheme for performing active remote sensing is to stare at an area with a single detector, while illuminating the area with one or more wavelengths of radiation. Various sources of noise, however, may lower the signal-to-noise ratio (SNR) of the measurement. Examples of such noise typically present in active remote sensing include solar background radiation, 1/f noise (i.e., noise whose power varies inversely with frequency), atmospheric turbulence, and/or scintillation.

Thus, there is a need in the art to perform active remote sensing while maintaining a high SNR.

SUMMARY OF THE INVENTION

Systems and processes consistent with the principles of the invention may include, among other things, modulating two signals at different frequencies before interaction with a sample of interest. A number of lock-in amplifiers may be used to process radiation detected from the sample at the different frequencies.

In accordance with one purpose of the invention as embodied and broadly described herein, a system for sensing a material in a sample may include a first source configured to emit first optical radiation over a range of wavelengths and a second source configured to emit second optical radiation at a fixed wavelength. A first modulator may be configured to modulate the first optical radiation at a first frequency to generate first modulated optical radiation, and a second modulator may be configured to modulate the second optical radiation at a second frequency different from the first frequency to generate second modulated optical radiation. The system may also include a first detector configured to detect the first and second modulated optical radiation after interaction with the sample and generate a first detection signal. A first lock-in amplifier may be configured to process the first detection signal based on the first frequency to produce a first output signal. A second lock-in amplifier may be configured to process the first detection signal based on the second frequency to produce a second output signal.

In another implementation consistent with principles of the invention, a method of remotely sensing a sample may include transmitting a beam of optical radiation toward the sample. The beam may include a varying component at a first frequency and a fixed component at a second frequency. The method may also include detecting the beam of optical radiation after interaction with the sample to produce a remote detection signal. A portion of the remote detection signal that is present at the first frequency may be determined, and another portion of the remote detection signal that is present at the second frequency may be determined. Information may be obtained about the sample based on the portion of the remote detection signal and the another portion of the remote detection signal.

In a further implementation consistent with principles of the invention, a system for sensing a characteristic of a sample may include a tunable source configured to emit optical radiation that varies over a wavelength range at a sweep frequency and a reference source configured to emit optical radiation at a reference wavelength. A first modulator may be configured to modulate the first optical radiation at a first frequency, and a second modulator may be configured to modulate the second optical radiation at a second frequency that is different from the first frequency and the sweep frequency. A science detector may be configured to detect the optical radiation from the first modulator and the second modulator after interaction with the sample and generate a science signal. A number of lock-in amplifiers may be respectively configured to generate components of the science signal that are present at the first and second frequencies. A processor may be configured to determine a characteristic of the sample based on the components of the science signal that are present at the first and second frequencies.

In a yet another implementation consistent with principles of the invention, a method of determining a concentration of a material in a sample may include modulating wavelength-varying radiation at a first frequency and modulating fixed-wavelength radiation at a second frequency. The wavelength-varying radiation and the fixed-wavelength radiation may be detected before interaction with the sample to produce a local detection signal. The method may also include transmitting the wavelength-varying radiation and the fixed-wavelength radiation to the sample. The wavelength-varying radiation and the fixed-wavelength radiation may be detected after interaction with the sample to produce a remote detection signal. The method may also include determining portions of the local detection signal and the remote detection signal at the first frequency, and determining portions of the local detection signal and the remote detection signal at the second frequency. A transmission profile may be obtained from the portions of the local detection signal and the remote detection signal at the first frequency and at the second frequency. The concentration of the material may be calculated based on the transmission profile.

BRIEF DESCRIPTION OF THE DRAWINGS

The accompanying drawings, which are incorporated in and constitute a part of this specification, illustrate an embodiment of the invention and, together with the description, explain the invention. In the drawings.

DETAILED DESCRIPTION

The following detailed description of the invention refers to the accompanying drawings. The same reference numbers may be used in different drawings to identify the same or similar elements. Also, the following detailed description does not limit the invention. Instead, the scope of the invention is defined by the appended claims and equivalents.

As described herein, in one implementation consistent with the principles of the invention, a remote sensing system may modulate a wavelength-varying signal at one frequency and a reference wavelength signal at a different frequency before interaction with a sample of interest. A number of lock-in amplifiers may be used to process radiation detected from the sample at the different frequencies.

EXEMPLARY SYSTEM

Figure 1:
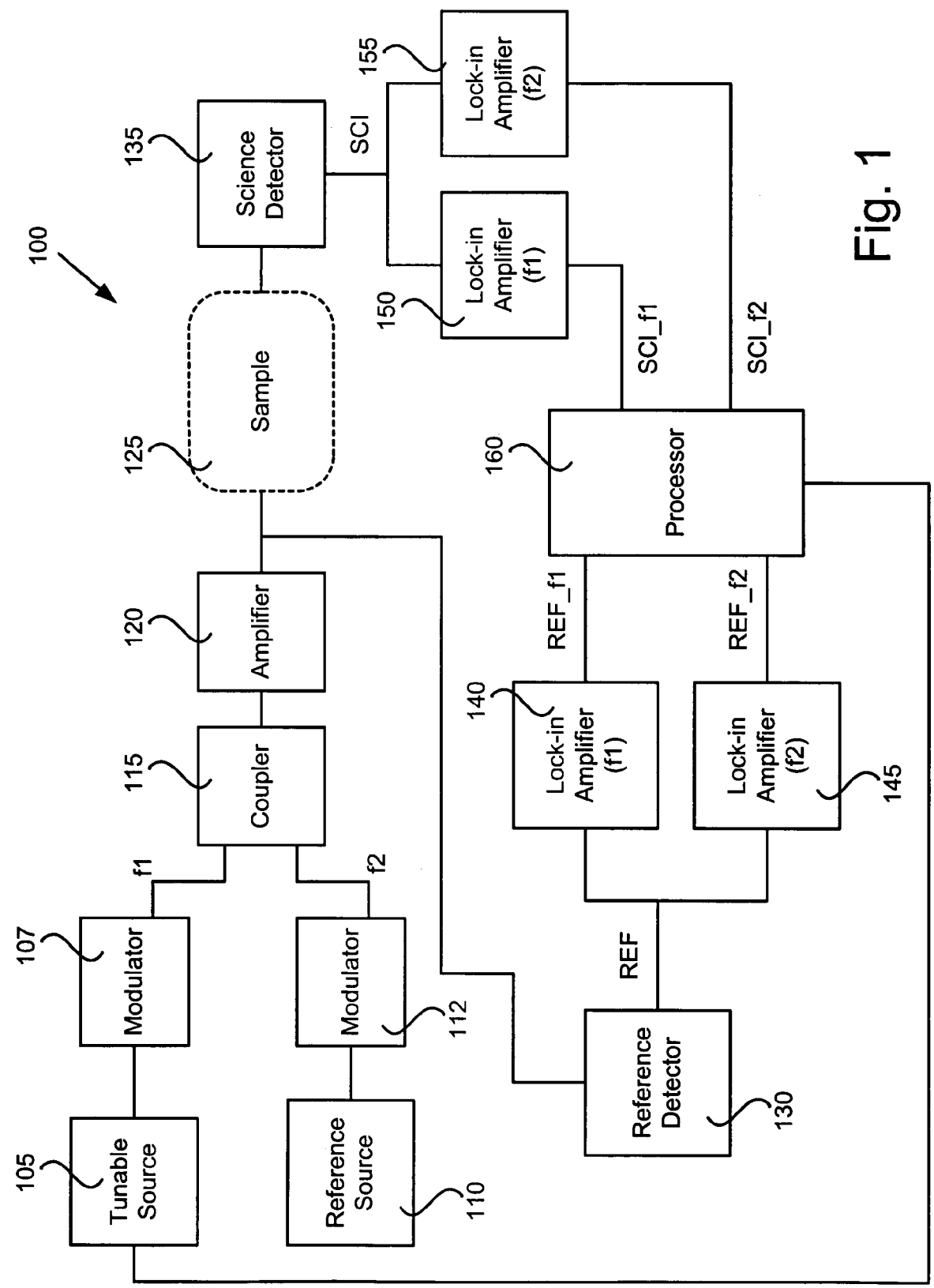
FIG. 1 is a schematic diagram of an active remote sensing system according to an implementation consistent with the principles of the invention.

FIG. 1 is a schematic diagram of an active remote sensing system 100 according to an implementation consistent with the principles of the invention. System 100 may include a tunable source 105, a first modulator 107, a reference source 110, a second modulator 112, a coupler 115, an amplifier 120, a sample 125, a reference detector 130, a science detector 135, first through fourth lock-in amplifiers 140/145/150/155, and a processor 160.

Tunable source 105 may include a source of optical or other radiation that is controlled to vary its output. Based on a control signal, tunable source 105 may emit radiation over a range of wavelengths $\lambda_{SWEEP}$. In one implementation consistent with the principles of the invention, tunable source 105 may be configured to continuously vary (or "sweep") its output wavelength over the range $\lambda_{SWEEP}$ at a sweep frequency. That is, tunable source 105 may repeat any given wavelength within the range $\lambda_{SWEEP}$ with a period that is the inverse of the sweep frequency. One exemplary sweep frequency is about 10 Hz, although this is merely an example and other sweep frequencies may be employed.

Figure 2:
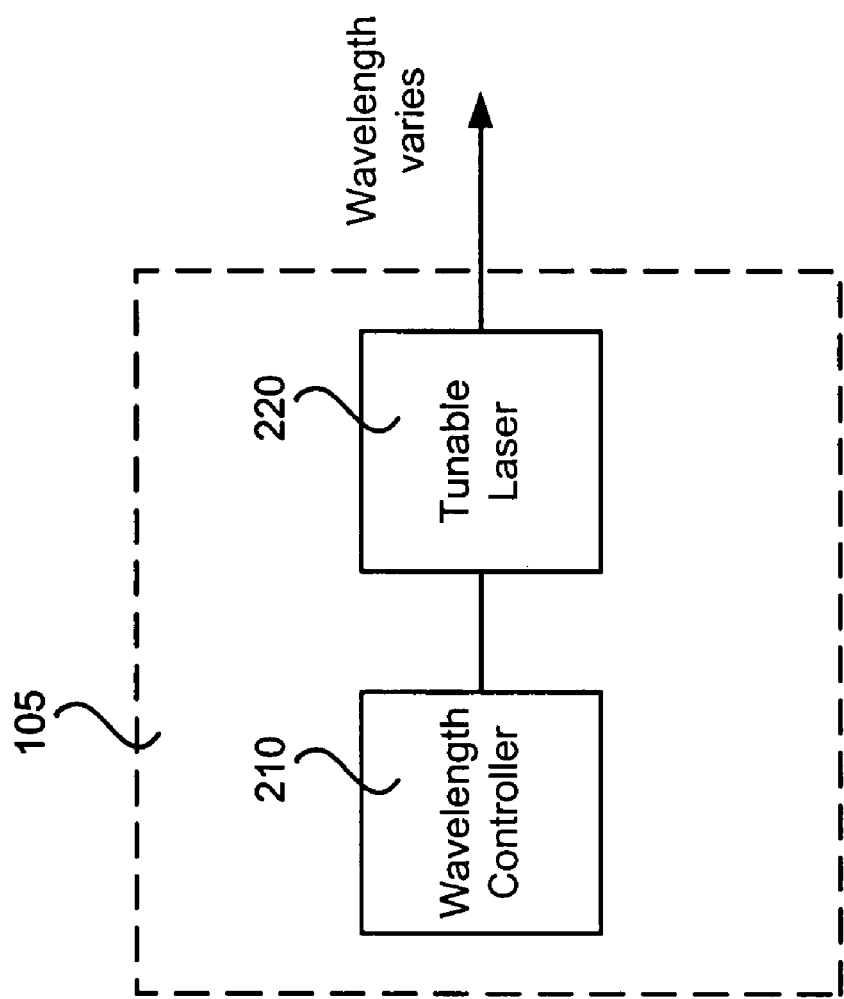
FIG. 2 illustrates an exemplary implementation of a tunable source in the remote sensing system of FIG. 1.

FIG. 2 is an exemplary configuration of tunable source 105. Tunable source 105 may include a wavelength controller 210 and a tunable laser 220 whose output is controlled by wavelength controller 210. Wavelength controller 210 may be configured to control the wavelengths produced by tunable laser 220, for example, by varying current that drives tunable laser 220 or by varying the temperature of tunable laser 220. In turn, wavelength controller 210 may receive feedback signals from tunable laser 220 to aid in its control. Wavelength controller 210 may produce a specific range of wavelengths (e.g., $\lambda_{SWEEP}$) based on input control signals that it receives (e.g., from processor 160 or other control circuitry (not shown)).

Tunable laser 220 may include, for example, a distributed feedback (DFB) laser that is precisely tunable in wavelength via a combination of temperature and current. Examples of such tunable lasers 220 include gas, solid, diode, and other types of lasers. Tunable laser 220 may alternately or additionally include a diode laser or an amplified diode laser. The wavelengths of the emitted radiation may fall in the ultraviolet, visible, short-wavelength infrared (SWIR), mid-wavelength infrared (MWIR), long-wavelength infrared (LWIR), or any other electromagnetic region suitable for active remote sensing. Optics (not shown) may be configured to direct the emitted radiation to first modulator 107.

Figure 3:
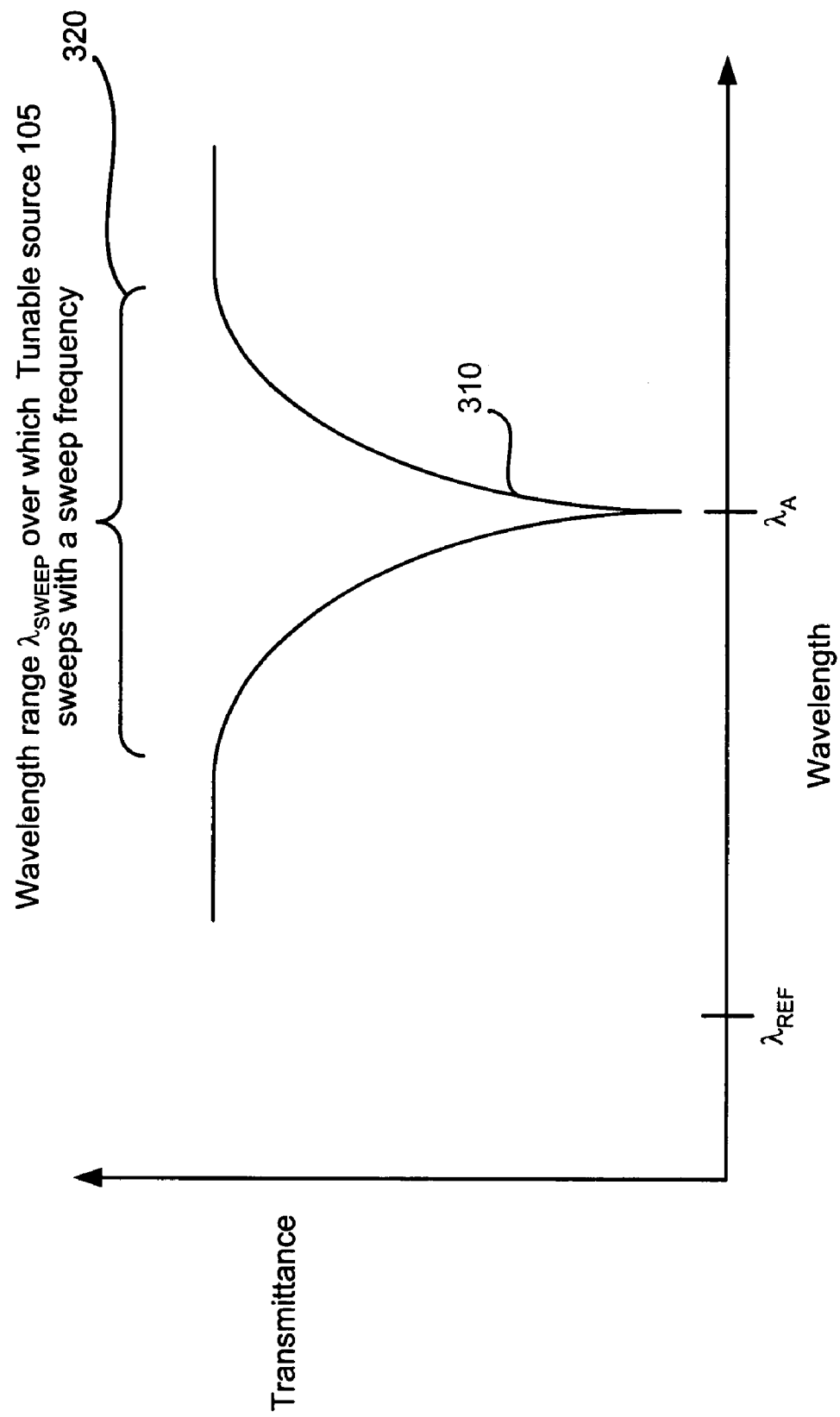
FIG. 3 is a plot illustrating an exemplary spectral feature of interest.

The operation of tunable source 105 in FIG. 2 may be further described with respect to FIG. 3. FIG. 3 is a plot of transmittance verses wavelength for an exemplary sample material illustrating an exemplary spectral feature of interest 310. In some implementations, the spectral feature of interest 310 may be an absorption feature and may be associated with a center absorption wavelength $\lambda_A$. Wavelength controller 210 may cause the output wavelength of tunable laser 220 to vary along wavelength range $\lambda_{SWEEP}$ 320 at some sweep frequency. Wavelength range $\lambda_{SWEEP}$ 320 may include the entire spectral feature of interest 310 and may extend to wavelengths on either side of spectral feature 310 (or may just extend far enough in wavelength to include spectral feature 310). Those skilled in the remote sensing art will understand how far beyond the spectral region occupied by spectral feature 310 wavelength range $\lambda_{SWEEP}$ 320 may extend.

Returning to FIG. 1, first modulator 107 may include an electro-optic (EO) modulator that is configured to impart a modulation at a first modulation frequency f1 to the output signal from tunable source 105. In one implementation consistent with the principles of the invention, first modulator 107 may impart an amplitude modulation to the output signal from tunable source 105. One exemplary first modulation frequency f1 may be about 5 kHz, although this is merely an example and other first modulation frequencies f1 may be employed.

Reference source 110 may include a source of optical or other radiation that is controlled to vary its output. Reference source 110 may emit radiation at a reference wavelength $\lambda_{REF}$. In one implementation consistent with the principles of the invention, reference source 110 may include, for example, a distributed feedback (DFB) laser that is precisely adjustable in wavelength via a combination of temperature and current. Examples of such reference lasers include gas, solid, diode, and other types of lasers. The wavelengths of the emitted radiation may fall in the ultraviolet, visible, short-wavelength infrared (SWIR), mid-wavelength infrared (MWIR), long-wavelength infrared (LWIR), or any other electromagnetic region suitable for active remote sensing. Optics (not shown) may be configured to direct the emitted radiation from reference source 110 to second modulator 112.

The operation of reference source 110 may be further described with respect to FIG. 3. In one implementation consistent with the principles of the invention, the reference wavelength $\lambda_{REF}$ of reference source 110 may fall outside the wavelength range $\lambda_{SWEEP}$ 320 of tunable source 105. In another implementation consistent with the principles of the invention, the reference wavelength $\lambda_{REF}$ of reference source 110 may fall inside the wavelength range $\lambda_{SWEEP}$ 320 of tunable source 105, but away from spectral feature 310.

Returning to FIG. 1, second modulator 112 may include an EO modulator that is configured to impart a modulation at a second modulation frequency f2 to the output signal from reference source 110. In one implementation consistent with the principles of the invention, second modulator 112 may impart an amplitude modulation to the output signal from reference source 110. In one implementation consistent with the principles of the invention, the second modulation frequency f2 imparted by second modulator 112 may be different from (and perhaps also not a harmonic of) the first modulation frequency f1 imparted by first modulator 107. An exemplary second modulation frequency f2 may be about 7.5 kHz, although this is merely an example and other modulation frequencies may be employed.

The proper choice of values for first modulation frequency f1 and second modulation frequency f2 may reduce overall noise in system 100. Values for first modulation frequency f1 and second modulation frequency f2 may also be selected to reduce mutual interference (e.g., inter-modulation). Those skilled in the art will understand in view of this disclosure that frequencies f1 and f2 may be chosen to optimize these and other parameters of system 100.

Coupler 115 may be configured to combine the output signals from first modulator 107 and second modulator 112 into a single output signal. In one implementation consistent with the principles of the invention, coupler 115 may be an optical fiber coupler and may receive the output signals from first modulator 107 and second modulator 112 via optical fibers. Although one example of coupler 115 is an optical fiber coupler, those skilled in the art will appreciate that coupler 115 may include any type of optical coupler. Although not strictly necessary for the operation of system 100, coupler 115 may ensure, for example, that the output signals from tunable source 105 and reference source 110 are transmitted with the same optical axis and field of view.

Amplifier 120 may be optionally used after coupler 115. If present, amplifier 120 may be configured to amplify the radiation from coupler 115. In one implementation consistent with the principles of the invention, amplifier 120 may include an erbium-doped fiber amplifier (EDFA) or similar optical amplifier. Although not shown, amplifier 120 may also include one or more of amplifier control circuitry and a beam expander. Those skilled in the art will recognize that various combinations of optical components may be used within amplifier 120 (and/or sources 105/110 and coupler 115) to achieve desired properties of the emitted radiation.

Sample 125 may include a material to be examined by laser spectroscopy. In one implementation, sample 125 may include a cell in, for example, a laboratory environment. In other implementations, sample 125 may include a volume of the atmosphere, which may or may not have a scattering background (e.g., the ground, for a down-looking system 100). Sample 125 may include a solid surface (e.g., the ground), objects (e.g., vehicles), vegetation, chemicals, gas/aerosol, or any other typical target of active remote sensing that has spectral features capable of spectral measurement. Sample 125 may include a substance having at least one absorption/reflection feature 310 around which tunable source 105 may be swept in wavelength.

The interaction between the output signal from tunable source 105 and sample 125 will now be described. Because the output signal from tunable source 105 is swept repeatedly in wavelength across the range $\lambda_{SWEEP}$ at a sweep frequency, its spectral interaction with sample 125 will also repeat at the sweep frequency. If sample 125 contains spectral feature 310 that absorbs/reflects over the region of interest, a portion of the output signal from tunable source 105 will be absorbed/reflected with a particular temporal pattern. This pattern may repeat at the sweep frequency.

The interaction between the output signal from reference source 110 and sample 125 will now be described. Because the output signal from reference source 110 is kept at a single reference wavelength $\lambda REF$, its spectral interaction with sample 125 may be considered constant. Thus, unlike the output signal from tunable source 105, the output signal from reference source 110 is not modulated by sample 125. The output signal from reference source 110, however, may retain its amplitude modulation at second modulation frequency f2 when passing through sample 125.

Because the output signal from tunable source 105 and the output signal from reference source 110 are joined by coupler 115, they may experience aspects of system 100 (e.g., amplifier 120) and sample 125 equally. Such common interaction between the signals enables "common mode" rejection of undesired signal perturbations. Any fluctuations unrelated to spectral feature 310 described above will be common to both output signal from tunable source 105 and the output signal from reference source 110. This knowledge may be used to eliminate unwanted fluctuations (i.e., noise) from the desired spectroscopic information about feature 310 in later processing.

After the combination of the output signal from tunable source 105 and the output signal from reference source 110 by coupler 115 (and any amplification by amplifier 120, if present), a small percentage (e.g., about 1%–5%) of the combined signal may be split off and imaged onto reference detector 130. Although not shown in FIG. 1, an optical tap or other suitable optical device may be used for this purpose prior to transmission of the combined signal to sample 125.

Reference detector 130 may be configured to convert an incident optical signal into a corresponding electrical signal, such as a digital signal. Reference detector 130 may include, for example, a high speed (i.e., high bandwidth) photodiode and/or signal conditioning circuitry, such as an analog-to-digital converter (ADC) that digitizes the electrical signal. In one implementation consistent with the principles of the invention, reference detector 130 may digitize the detected signal at a rate above (e.g., 10 times faster than) a desired information rate (e.g., the greater of first modulation frequency f1 and second modulation frequency f2).

Reference detector 130 may output an electrical, reference signal (REF). Because the REF signal is generated before interaction with sample 125, it may provide a baseline for comparison with another detected signal, as will be understood by those skilled in the remote sensing art.

Science detector 135 may detect optical radiation reflected from or transmitted through sample 125. Science detector 135 may be configured to convert received optical energy into an electrical signal, such as a digital signal, which may be calibrated to correspond to the optical energy by processor 160. Similar to reference detector 130, science detector 135 may include a high speed (i.e., high bandwidth) photodiode and/or signal conditioning circuitry.

Science detector 135 may output an electrical, science signal (SCI). Because the SCI signal is generated after interaction with sample 125, it may yield one or more spectral characteristics of sample 125 when processed (e.g., in conjunction with the REF signal), as will be described in greater detail below.

First lock-in amplifier 140 may be configured to receive the REF signal from reference detector 130 and perform "phase-sensitive" detection upon the REF signal at an operational frequency f1. The operational frequency f1 of first lock-in amplifier 140 may be selected to be the same as the first modulation frequency f1 of first modulator 107. Those skilled in the electrical arts will be familiar with the operation and construction of lock-in amplifiers (e.g., including tuned filters, mixers, phase shifters, and low pass filters, or similar functions in a digital signal processor (DSP)). In one implementation consistent with the principles of the invention, first lock-in amplifier 140 may operate on a digital REF signal from reference detector 130 via an internal DSP, and may be configured to receive an external reference signal at first modulation frequency f1 (not shown) from tunable source 105 or processor 160.

As those skilled in the art will appreciate, the operational/sweep frequency f1 of first lock-in amplifier 140 and tunable source 105 may be selected to be high enough to significantly reduce 1/f noise that may be present in the radiation emitted by tunable source 105. First lock-in amplifier 140 may output a first signal REF_f1 to processor 160 that corresponds to a portion of the REF signal present at the first modulation frequency f1 (i.e., the portion from tunable source 105).

Second lock-in amplifier 145 may be configured to receive the REF signal from reference detector 130 and perform "phase-sensitive" detection upon the REF signal at an operational frequency f2. The operational frequency f2 of second lock-in amplifier 145 may be selected to be the same as the second modulation frequency f2 of second modulator 112. In one implementation consistent with the principles of the invention, second lock-in amplifier 145 may operate on a digital REF signal from reference detector 130 via an internal DSP, and may be configured to receive an external reference signal at second modulation frequency f2 (not shown) from reference source 110 or processor 160.

As those skilled in the art will appreciate, the operational/modulation frequency f2 of second lock-in amplifier 145 and reference source 110 may be selected to be high enough to significantly reduce 1/f noise that may be present in the radiation emitted by reference source 110. Second lock-in amplifier 145 may output a first signal REF_f2 to processor 160 that corresponds to a portion of the REF signal present at the second modulation frequency f2 (i.e., the portion from reference source 110).

Third lock-in amplifier 150 and fourth lock-in amplifier 155 may be configured similar to first lock-in amplifier 140 and second lock-in amplifier 145, respectively. Third lock-in amplifier 150 may output a third signal SCI_f1 to processor 160 that corresponds to a portion of the SCI signal output by science detector 135 that is present at the first modulation frequency f1 (i.e., the portion from tunable source 105). Fourth lock-in amplifier 155 may output a fourth signal SCI_f2 to processor 160 that corresponds to a portion of the SCI signal output by science detector 135 that is present at the second modulation frequency f2 (i.e., the portion from reference source 110). Further, a relatively narrow bandwidth about the respective operational frequencies of third and fourth lock-in amplifiers 150/155 may remove a significant amount of noise from sources other than tunable source 105 and reference source 110, such as solar background radiation. Hence, use of third and fourth lock-in amplifiers 150/155 may significantly increase the SNR of the radiation detected by science detector 135.

Figure 4:
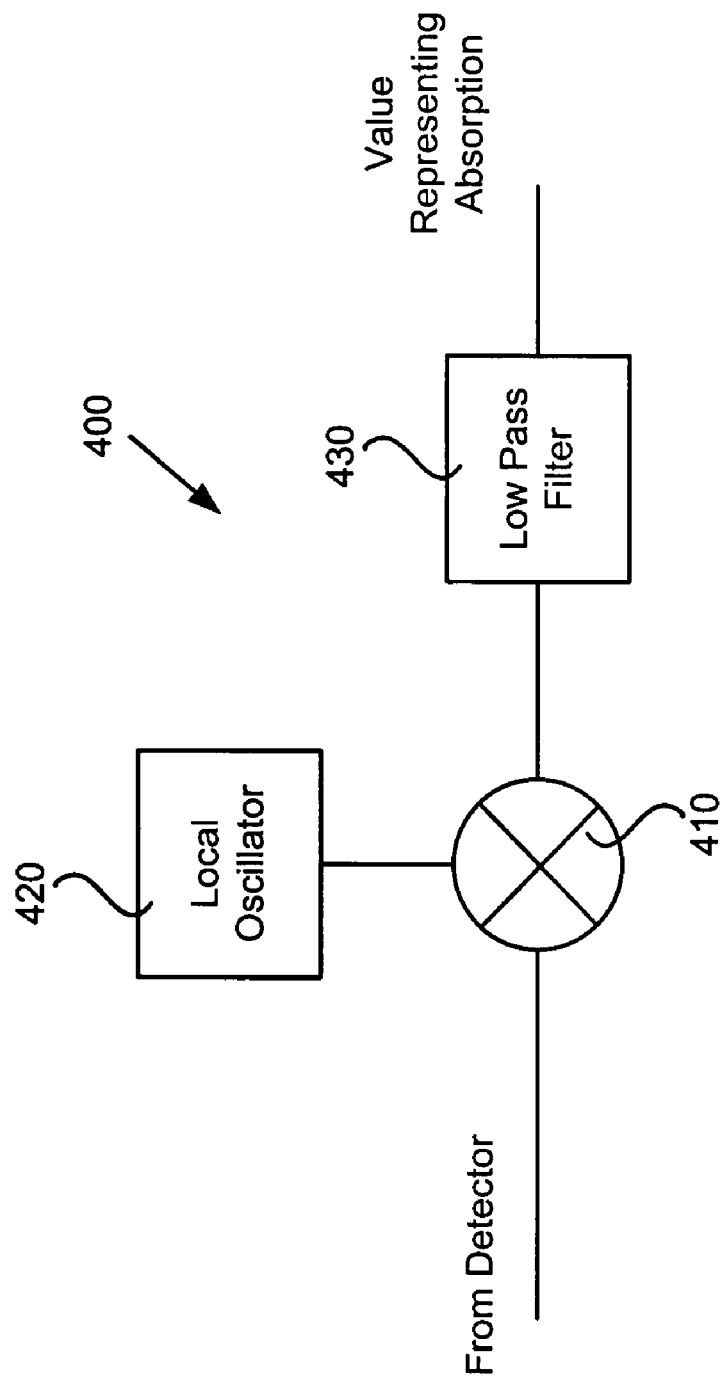
FIG. 4 illustrates an alternate device to replace ones of the lock-in amplifiers in the remote sensing system of FIG. 1.

FIG. 4 is an alternate device 400 that may be used in place of one or more of first through fourth lock-in amplifiers 140/145/150/155 in remote sensing system 100. Device 400 may include a mixer 410, a local oscillator 420, and a low pass filter 430. Mixer 410 may be configured to receive and combine (e.g., by multiplication) a signal from a detector and an output of local oscillator 420. Local oscillator 420 may be configured to generate an output signal that has the same shape as an absorption feature (e.g., spectral feature 310) in the spectral region of interest (e.g., wavelength range $\lambda_{SWEEP}$). It should be noted that the output signal of local oscillator 420 need not have the same shape as the absorption feature. For example, acceptable results may be obtained using a sine wave (e.g., at first modulation frequency f1) as the output signal of local oscillator 420. Low pass filter 430 may filter out higher frequencies in the output of mixer 410 to produce a value that represents absorption. Each of mixer 410, local oscillator 420, and low pass filter 430 may be digitally implemented, for example as algorithms within a DSP device.

Returning to FIG. 1, processor 160 may include circuitry to read, format, and/or store data from lock-in amplifiers 140/145/150/155. In one implementation consistent with the principles of the invention, processor 160 stores all data read from lock-in amplifiers 140/145/150/155 for retrieval and processing at a later date. Processor 160 may include one or more shift registers in such an implementation. In other implementations, processor 160 may process the data from lock-in amplifiers 140/145/150/155, rather than merely storing "raw" data. For example, processor 160 may combine REF_f1, REF_f2, SCI_f1, and SCI_f2 from lock-in amplifiers 140/145/150/155 to obtain the amount of absorption over the spectral region of interest (e.g., wavelength range $\lambda_{SWEEP}$) and/or the material concentration in sample 125, as will be described in greater detail below. In other implementations, processor 160 may include a communication link (e.g., a wireless communication link) for transferring raw or processed data from lock-in amplifiers 140/145/150/155 to a remote location.

Processor 160 may also be configured to control the first modulation frequency f1 of first modulator 107, and processor 160 may provide an external reference signal at this first modulation frequency f1 to first and third lock-in amplifiers 140/150. Similarly, processor 160 may be configured to control the second modulation frequency f2 of second modulator 112, and processor 160 may provide an external reference signal at this second modulation frequency f2 to second and fourth lock-in amplifiers 145/155.

Processor 160 may, or may not, include a wavelength calibration device (not shown) for calibrating wavelength across the range $\lambda_{SWEEP}$. Examples of the wavelength calibration device may include a Sweepmeter™ (produced by Precision Photonics), an etalon, an HP® wavemeter, a fast interferometer, or other suitable tools for calibrating wavelength. When using such a wavelength calibration device, an absolute wavelength reference may be provided, and more exact results may be extracted. Such a wavelength calibration device may facilitate more exact scientific measurements, but may not be needed for a fieldable system 100. Without a wavelength calibration device, for example, the relative performance may still be equivalent to having a wavelength calibration device, but the results obtained may be off from an "exact" or "true" value by some offset or gain factor. This offset or gain factor may be removed by calibration processing. Not including the wavelength calibration device may make system 100 easier to implement.

PROCESS OF OBTAINING DATA

Figure 5:
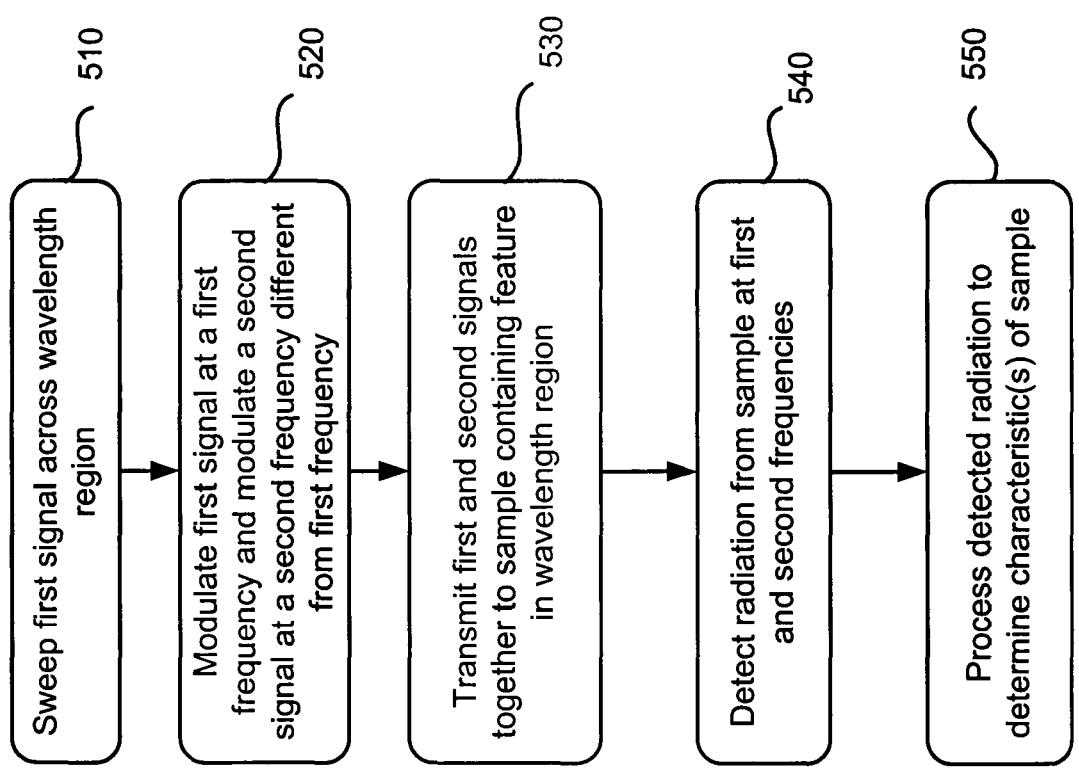
FIG. 5 is flow chart illustrating a process of actively sensing information on a spectral feature within a wavelength range according to an implementation consistent with the present invention.

FIG. 5 is flow chart illustrating a process of actively sensing information on a spectral feature (e.g., spectral feature of interest 310 centered on absorption wavelength $\lambda_A$) within a wavelength range (e.g., $\lambda_{SWEEP}$ 320) according to an implementation consistent with the present invention. The process may begin with tunable source 105 periodically emitting first radiation along the wavelength range $\lambda_{SWEEP}$ [act 510]. In one implementation, tunable source 105 may repeatedly traverse the wavelength range $\lambda_{SWEEP}$.

The first radiation from tunable source 105 may be amplitude modulated at a first modulation frequency f1, and second radiation from reference source 110 may be amplitude modulated at a second modulation frequency f2 that is different from the first modulation frequency f1 [act 520]. In one implementation, reference source 110 may emit the second radiation at a reference wavelength $\lambda_{REF}$ that is outside the wavelength range $\lambda_{SWEEP}$ of the first radiation from tunable source 105.

Processing may continue by transmitting the differently-modulated first and second radiation together to sample 125 [act 530]. In one implementation consistent with the principles of the invention, the differently-modulated first and second radiation may be combined by coupler 115 and optionally amplified by amplifier 120 prior to transmission. Sample 125 may contain a spectral feature of interest 310 within the wavelength range $\lambda_{SWEEP}$ of the first radiation. The differently-modulated first and second radiation respectively remain amplitude modulated at first modulation frequency f1 and the second modulation frequency f2 after interacting with sample 125.

Processing may continue with third and fourth lock-in amplifiers 150/155, in conjunction with science detector 135, respectively detecting radiation from sample 125 at the first modulation frequency f1 and the second modulation frequency f2 [act 540]. Thus, third lock-in amplifier 150 may extract information SCI_f1 at modulation frequency f1 that corresponds to the first radiation from tunable source 105. Fourth lock-in amplifier 155 may extract information SCI_f2 at second modulation frequency f2 that corresponds to the second (reference) radiation from reference source 110. In one implementation consistent with the principles of the invention, first and second lock-in amplifiers 140/145, in conjunction with reference detector 130, may respectively detect radiation at the first modulation frequency f1 (i.e., REF_f1) and the second modulation frequency f2 (i.e., REF_f2) before interaction with the sample 125.

The detected information SCI_f1 and SCI_f2 (possibly in conjunction with REF_f1 and REF_f2) may be processed by processor 160 to determine characteristics of sample 125 [act 550]. Further theoretical and experimental details of the processing in act 150 will be given below. The above-described spectral lock-in technique uses lock-in signal recovery techniques to perform spectral sensing, such as total-column gas concentration retrieval. This technique permits real time processing and very high data rates. Advantageously, the above-described scheme may improve the measurement SNR relative to other methods of gathering spectral data.

EXEMPLARY DATA PROCESSING SCHEME

One exemplary data processing scheme that may be used in act 550 is as follows. Although the following scheme is intended to find the concentration of an absorbing material (e.g., a gas) in sample 125, those skilled in the art will appreciate that other processing schemes are possible. The transmission of light through an absorbing medium as a function of frequency, T(v), is described by the Beer-Lambert law:

$$T(v) = \exp(-\int N(r) \cdot \sigma(v) \cdot dr) \quad (1)$$

N(r) in Eqn. 1 is a spatially varying number density of the absorbing material in the measurement volume, σ(v) is the frequency dependent cross-section for absorption, and r is the path over which the measurement is made. The cross-section for absorption σ(v) for a material may be related to the strength of the absorption and the transition lineshape by:

$$\sigma(v) = S(T) \cdot g(v) \quad (2)$$

S(T) in Eqn. 2 is temperature dependent line strength, and g(v) is the area-normalized lineshape for the material of interest.

To find the total density of absorbers in the measurement volume (i.e. the total column density), Eqns. 1 and 2 may be expressed, after taking the natural log of both sides, by:

$$-\ln[T(v)] = N \cdot S(T) \cdot g(v) \int_0^l dr = N \cdot S(T) \cdot g(v) \cdot l \quad (3)$$

The total column density, N*l, of the material of interest may then be expressed as:

$$N \cdot l = -\frac{\ln[T(v)]}{S(T) \cdot g(v)} \quad (4)$$

By scanning the wavelength of a laser (e.g., $\lambda_{SWEEP}$) across an absorption peak (e.g., spectral feature 310), a profile of the transmission can be obtained. With knowledge of the line strength S(T), such a profile may be related to the column density of the absorbing material.

With reference to FIG. 1, the transmission, T(v), may be obtained from the four signals output from lock-in amplifiers 140/145/150/155, namely REF_f1, REF_f2, SCI_f1, and SCI_f2. These four output signals may be characterized/renamed as follows:

| | |
|---|---|
| Swept Transmitted (SWT) | (i.e., SCI_f1, an absorption profile across $\lambda_{SWEEP}$) |
| Swept Reference (SWR) | (i.e., REF_f1, a normalization of swept power) |
| Static Transmitted (STT) | (i.e., SCI_f2, used to eliminate atmospheric fluctuations) |
| Static Reference (STR) | (i.e., REF_f2, a normalization of static power) |

The transmission, T(v), may be derived from the following:

$$\text{Signal} = \frac{SWT \cdot STR}{SWR \cdot STT} = \frac{SCI\_f1 \cdot REF\_f2}{REF\_f1 \cdot SCI\_f2} \quad (5)$$

By sweeping tunable source 105 across $\lambda_{SWEEP}$, a profile of signal transmission as a function of wavenumber (i.e., Signal) may be obtained. Some number of Signal sweeps across $\lambda_{SWEEP}$ may then be averaged (e.g., 100 Signals). One example of such averaged Signal data appears in FIG. 6. This averaged Signal data may then be fit with a cubic polynomial to describe a Baseline for the data (e.g., the line through the data in FIG. 6). A Lorentzian peak function (not shown) may also be fit to the averaged Signal data to describe the lineshape (i.e., a Fit) associated with the data.

Once the Baseline and the Fit have been generated for the averaged Signal data, a normalized transmission profile, T(v), may be obtained as follows:

$$T = \frac{\text{Fit}}{\text{Baseline}} \qquad (6)$$

Figure 7:
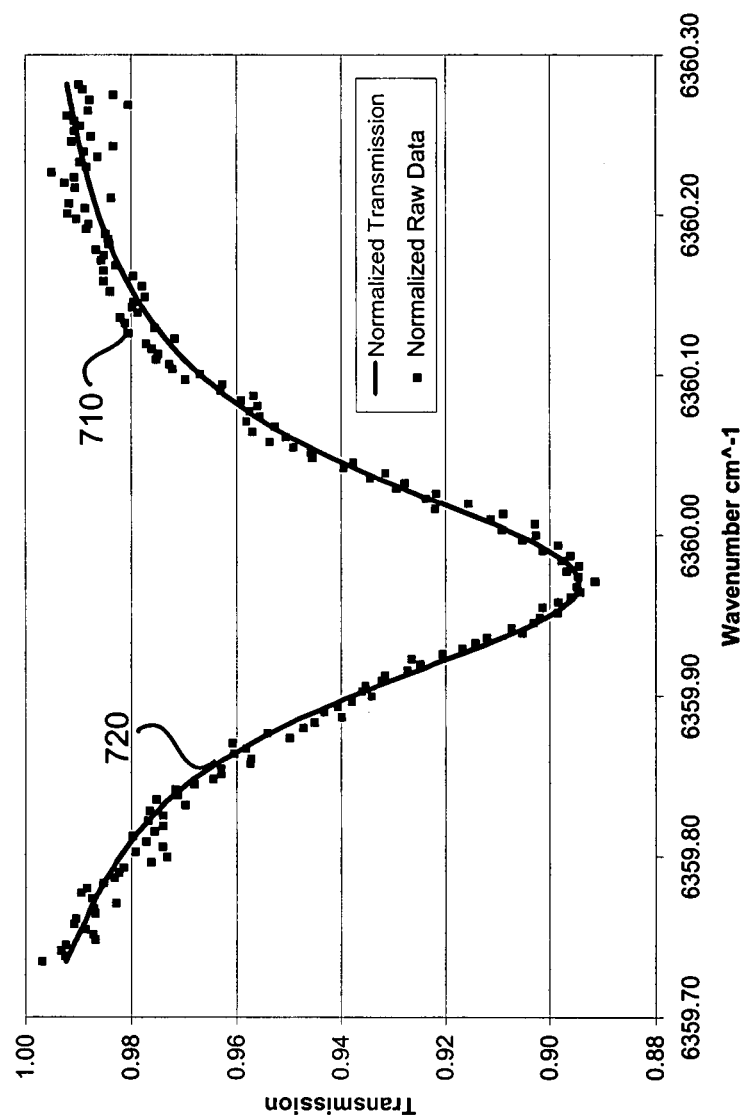
FIG. 7 is a plot of normalized signal data and a normalized transmission curve fit to the data according to an implementation consistent with the principles of the invention.

In other words, the normalized transmission profile, T(v), may be obtained by normalizing the Fit lineshape by the Baseline for the data. FIG. 7 illustrates one example of such a normalized transmission profile, T(v), generated in the above-described manner.

Using this normalized profile of transmission as a function of wavenumber, T(v), the total column density of the absorbing material in sample 125 may be obtained from Eqn. 4 (i.e., by using T(v) to compute N·l). The total column density may be converted to a concentration in ppm*m as follows:

$$C = \frac{N \cdot l}{D} \cdot 1 \times 10^4 \qquad (7)$$

N in Eqn. 7 is density of the absorbing material in molecules/$cm^3$, l is path length in cm, C is concentration, D is the density of the atmosphere in molecules/$cm^3$, and the constant is to convert parts-centimeter to ppm-m. In this manner, the concentration, C, of an absorbing material (e.g., a gas) in sample 125 may be found using system 100.

EXEMPLARY OPERATION OF SYSTEM

System 100 may be used for standoff, open path, atmospheric monitoring of a material in an atmospheric sample 125. Data collection was performed to detect carbon dioxide ($CO_2$) gas using system 100, and exemplary system parameters and results are presented below to illustrate the usefulness of system 100 and its remote sensing scheme. It should be understood, however, that the values below are purely exemplary, and should not be construed to limit the components of system 100 or their equivalents in any way.

In system 100, one CW DFB laser diode 105 was swept across an absorption feature (i.e., a $CO_2$ absorption line at 6359.9678 $cm^{-1}$). The $CO_2$ absorption line at 6359.9678 $cm^{-1}$ has a strength of $1.844 \times 10^{-23}$ $cm^2$/molecule at 296 K and an air broadening half-width of 0.07340-$cm^{-1}$ at 1 atmosphere. Another CW DFB laser diode 110 was set at a fixed wavelength off the absorption band (i.e., 6346 $cm^{-1}$). Diode 105 was swept at a rate of 10 Hz. Each wavelength sweep covered approximately 0.5 $cm^{-1}$. The ratio of the swept to the fixed signal eliminates unwanted time varying atmospheric fluctuations.

A data acquisition (DAQ) system (including or connected to processor 160) was to take data at points along the wavelength sweep that were equally spaced in wavelength (i.e., 0.8 pm). Distinct modulation signatures were imposed upon the two laser signals by EO modulators 107/112, allowing the swept and reference signals from diodes 105/110 to be differentiated from other sources of radiation and from one another. These signals were combined optically via coupler 115 and amplified by an erbium doped fiber amplifier (EDFA) 120 operating at 1.5-$\mu$m.

A 2% reference signal was split off after EDFA 120. The remaining 98% was transmitted into the region of the atmosphere to be monitored (i.e., sample 125). In the trial, an 8" athermal, IR, fiber-coupled telescope was used to collect the return signal from sample 125. The 2% reference signal and the received return signal were both imaged onto uncooled fiber-coupled detectors 130/135 and amplified by SR570 current amplifiers. These signals were then processed by four DSP lock-in amplifiers 140/145/150/155. Lock-in amplifiers 140/145/150/155 recovered the swept and static portions of the reference and transmitted signals using their distinct modulation signatures imparted by EO modulators 107/112.

Figure 6:
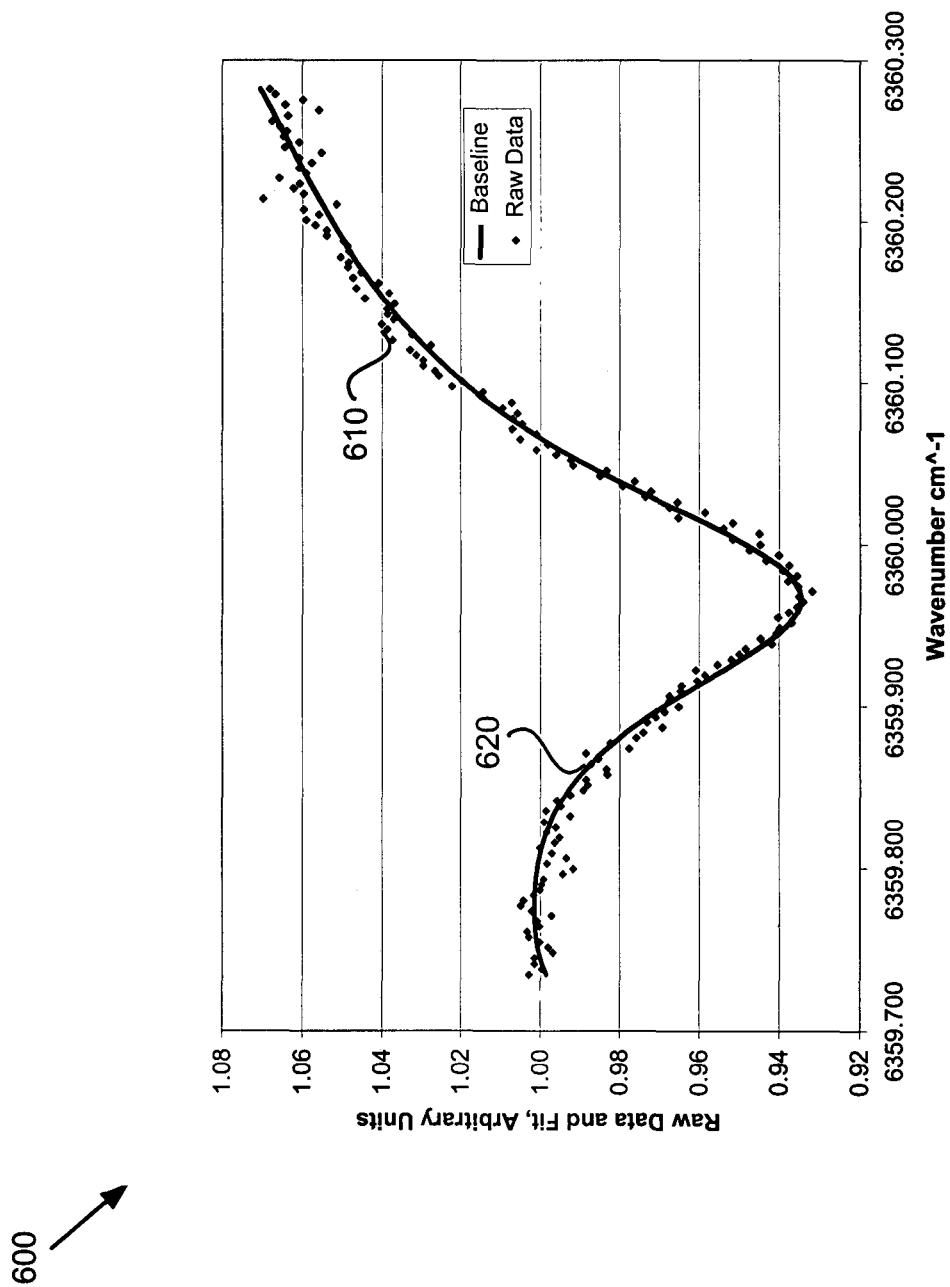
FIG. 6 is a plot of signal data and a baseline curve fit to the data according to an implementation consistent with the principles of the invention.

Collected data was averaged over 100 cycles to obtain a single sweep at a data rate of 0.1 Hz. FIG. 6 is a plot 600 of such averaged signal data 610 and a baseline curve 620 that was fit to data 610 according to the above-described data processing scheme. Similarly, FIG. 7 is a plot 700 of normalized signal data 710 and a normalized transmission curve 720 obtained according to the above-described data processing scheme.

Under the trial conditions, system 100 achieved a sensitivity of 28-ppm over 1.5 km of open air with 200 pW of received power, a 10 second acquisition time, and a peak absorption cross section of $8 \times 10^{-23}$. This 28-ppm sensitivity corresponds to a standard error in fractional absorbance of $7 \times 10^{-3}$. These open-air results from system 100 have been achieved using space qualified laser components 105/110, uncooled InGaAs detectors 130/135, and off the shelf electronics in a rugged all fiber architecture. By way of comparison, closed cell lab sensitivities may be better than 3000 ppm*m, with a 1 Hz data rate and a standard error in fractional absorbance of $5 \times 10^{-4}$. In the lab, the 1.5 km open path and telescope were replaced with a multipass gas cell with an effective path length of 22 m, and a 1" collecting lens.

Figure 8:
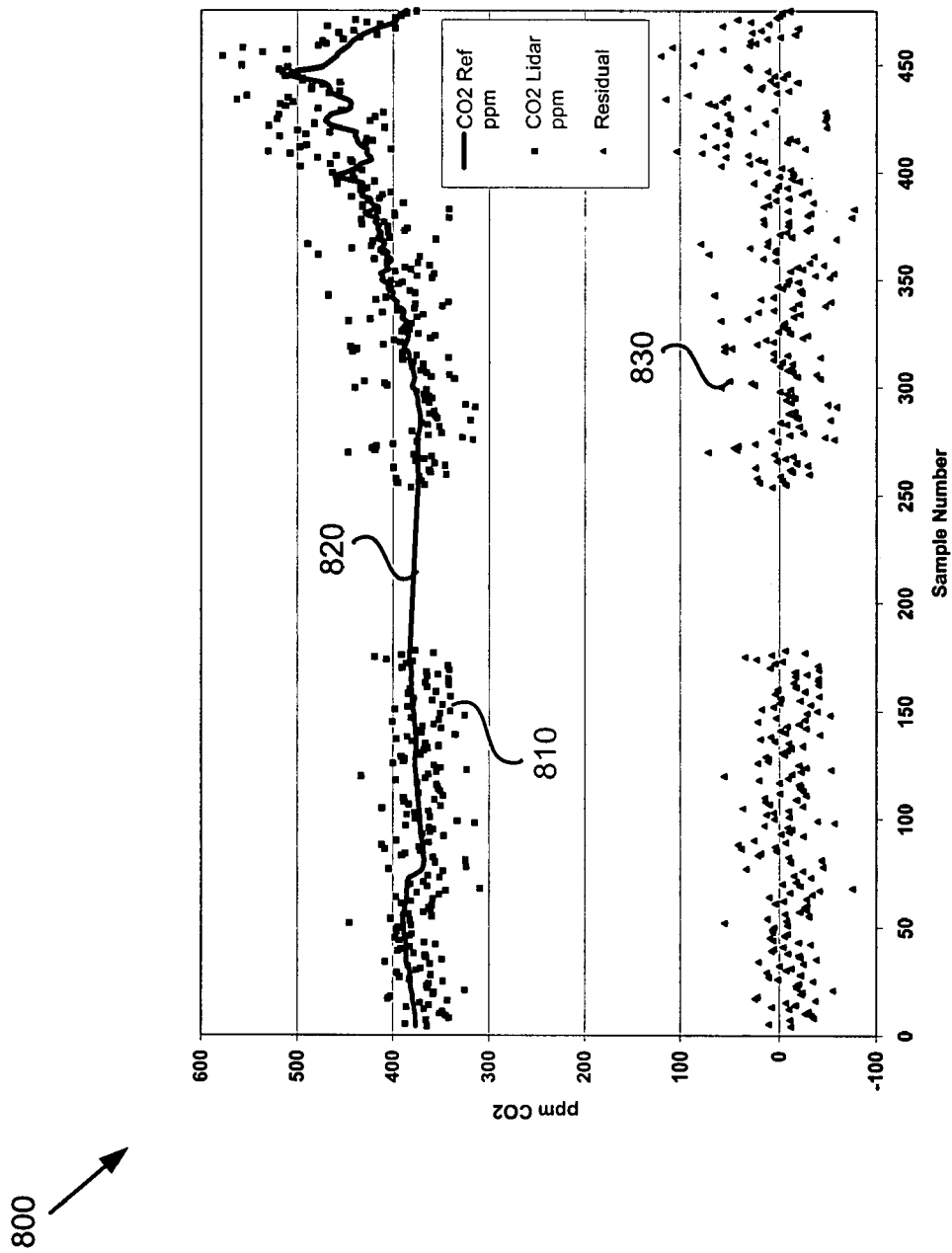
FIG. 8 is a plot of collected concentration data and laboratory concentration data according to an implementation consistent with the principles of the invention.

FIG. 8 is a plot 800 of collected concentration data 810 and laboratory (reference) concentration data 820 according to an implementation consistent with the principles of the invention. Residual concentration data 830 are also shown. Residual concentration data 830 are obtained by subtracting collected concentration data 810 from laboratory concentration data 820. The gap in FIG. 8 that is apparent in collected concentration data 810 and residual concentration data 830 around sample numbers 200–250 is due solely to corruption of data taken during the trial. Collected concentration data 810 agrees with laboratory concentration data 820 to an accuracy of 28 ppm (i.e., the standard deviation of the residual b concentration data 830) over a path of 1.5 km in the open atmosphere. This accuracy corresponds to an error in fractional absorbance of $7 \times 10^{-3}$.

Possible sources of sensitivity degradation for system 100 may be low received power and turbulence in the atmosphere. Given increased transmitted power (most likely due to amplifier 120) and/or greater line strength of the material of interest in sample 125, better sensitivities may be achieved. In the trial, 200 mW of laser power was transmitted and only 200 pW reached the detector 135. This is very near the noise floor of the un-cooled InGaAs detectors that were used. Better detector technology and higher laser output power will provide better chemical detection sensitivity. EDFAs are currently capable of delivering 5W, and detector amplifier combinations may be employed with orders of magnitude increases in performance. For chemicals having low natural abundance, or that do not occur naturally, increases in concentration sensitivity may be linear with increases in line strength as suggested by Eqn. 4.

A field deployable, turn key system 100 has been developed for standoff monitoring material (e.g., $CO_2$) concentrations in real time with a data rate of up to around 1 Hz. System 100 may employ space-qualified lasers 10/110 and commercial off the shelf (COTS) components. The entire system 100 may be miniaturized using DSP and FPGA technology.

CONCLUSION

Systems and methods consistent with the principles of the invention may modulate a wavelength-varying signal at one frequency and a reference wavelength signal at a different frequency before interaction with a sample of interest. A number of lock-in amplifiers may be used to process radiation detected from the sample at the different frequencies.

The foregoing description of preferred embodiments of the present invention provides illustration and description, but is not intended to be exhaustive or to limit the invention to the precise form disclosed. Modifications and variations are possible in light of the above teachings or may be acquired from practice of the invention.

For example, some factors that determine the applicability of the techniques described herein are the wavelengths (e.g., spectral features) that may be monitored, the rate at which concentrations may be reported, and the sensitivities that may be achieved. Spectral features may be limited to lines that can be reached with current EDFA technology (e.g., 1529 nm to 1620 nm operational range). With the introduction of QCL lasers and midwave fibers, however, wider wavelength regions may be encompassed by the scalable techniques described herein. Without amplifier 120, or with different amplifier technology, the technique described herein may be implemented using any currently-existing or later-developed tunable-wavelength laser (and corresponding wavelength range $\lambda_{SWEEP}$ of such laser). Data rate may be limited by the ability to sweep tunable source 105 quickly in wavelength. Using various techniques and equipment, data rates in excess of 500 Hz may be achieved. Sensitivities may be primarily governed by output power and/or detector/amplifier technology. As mentioned previously, detectors with much smaller dark current and EDFAs having 5 W of output power may be used to improve the sensitivity of system 100.

Further, additional channels may be used in system 100. For example, one or more additional swept laser, modulator, detector, and lock-in amplifier configurations may be added to sweep (in wavelength) one or more additional features of interest within sample 125. Hence, system 100 is not limited to the exact number of sources and detectors illustrated in FIG. 1, as will be understood by those skilled in the art in view of this disclosure.

Also, the phase sensitive detection technique described herein may be used in multiple sensing scenarios. For example, it may be used to: probe areas or materials for concentrations of certain chemicals; determine the presence of harmful chemicals in civilian areas; monitor environmental processes; monitor industrial processes; monitor industrial environments; find and track chemicals in air/water; provide early warning of threats; and/or any other detection scenario that those skilled in the art may envision involving one or more spectral features of interest. Although system 100 has been tested with a horizontal total path of 1.5 km, it is scalable to airborne and space-based applications and distances.

Moreover, the acts in FIG. 5 need not be implemented in the order shown; nor do all of the acts need to be performed. Also, those acts which are not dependent on other acts may be performed in parallel. Further, the acts in these figures may be implemented as instructions, or groups of instructions, in a computer-readable medium.

No element, act, or instruction used in the description of the present application should be construed as critical or essential to the invention unless explicitly described as such. Also, as used herein, the article "a" is intended to include one or more items. Where only one item is intended, the term "one" or similar language is used. The scope of the invention is defined by the claims and their equivalents.

What is claimed:

1. A system for sensing a material in a sample, comprising:
   a first source configured to emit first optical radiation over a range of wavelengths;
   a second source configured to emit second optical radiation at a fixed wavelength;
   a first modulator configured to modulate the first optical radiation at a first frequency to generate first modulated optical radiation;
   a second modulator configured to modulate the second optical radiation at a second frequency not harmonically related to and different from the first frequency to generate second modulated optical radiation;
   a first detector configured to detect the first and second modulated optical radiation scattered/reflected from the sample and generate a first detection signal;
   a first lock-in amplifier configured to process the first detection signal based on the first frequency to produce a first output signal; and
   a second lock-in amplifier configured to process the first detection signal based on the second frequency to produce a second output signal.

2. The system of claim 1, wherein the first source includes a distributed feedback (DFB) laser.

3. The system of claim 1, further comprising:
   a coupler connected to the first modulator and the second modulator configured to combine the first modulated optical radiation into a combined signal; and
   an optical amplifier connected to the coupler and configured to amplify the combined signal.

4. The system of claim 1, further comprising:
   a second detector configured to detect the first and second modulated optical radiation before interaction with the sample and generate a second detection signal;
   a third lock-in amplifier configured to process the second detection signal based on the first frequency to produce a third output signal; and
   a fourth lock-in amplifier configured to process the second detection signal based on the second frequency to produce a fourth output signal.

5. The system of claim 4, wherein material in the sample produces a spectral feature within the range of wavelengths, the system further comprising:
   a processor configured to process the first output signal, the second output signal, the third output signal, and the fourth output signal to obtain information relating to the spectral feature.

6. The system of claim 5, wherein the information includes a concentration of the material in the sample.

7. A method of remotely sensing a sample, comprising:
   transmitting a beam of optical radiation toward the sample, the beam including an amplitude modulated component at a first frequency and another amplitude modulated component at a second frequency, wherein the first frequency is not harmonically related to and is different from the second frequency;
   detecting the beam of optical radiation after scattering/reflecting from the sample to produce a remote detection signal;
   determining a portion of the remote detection signal that is present at the first frequency;

determining another portion of the remote detection signal that is present at the second frequency; and obtaining information about the sample based on the portion of the remote detection signal and the portion of the remote detection signal.

8. The method of claim 7, further comprising:

generating a tuning signal that periodically sweeps over a range of wavelengths at a sweep frequency;

generating a reference signal having a reference wavelength;

modulating the tuning signal at the first frequency to produce the amplitude modulation at the first frequency;

modulating the reference signal at the second frequency to produce the amplitude modulation at the second frequency; and combining the tuning signal and the reference signal into the beam of optical radiation.

9. The method of claim 8, further comprising:

amplifying the beam of optical radiation before the transmitting.

10. The method of claim 7, further comprising:

detecting the beam of optical radiation before scattering/reflecting from the sample to produce a local detection signal;

determining a portion of the local detection signal that is present at the first frequency; and determining another portion of the local detection signal that is present at the second frequency.

11. The method of claim 7, wherein the obtaining includes:

obtaining information about the sample based on the portion of the local detection signal and the other portion of the local detection signal.

12. A system for sensing a characteristic of a sample, comprising:

a tunable wavelength source configured to emit first optical radiation that varies over a wavelength range at a sweep frequency;

a reference source configured to emit second optical radiation at a fixed reference wavelength;

a first modulator configured to modulate the first optical radiation at a first frequency;

a second modulator configured to modulate the second optical radiation at a second frequency that is different from the first frequency and the sweep frequency, and is not harmonically related to the first frequency;

a science detector configured to detect the optical radiation from the first modulator and the second modulator after scattering/reflecting from the sample and generate a science signal;

a plurality of lock-in amplifiers respectively configured to generate components of the science signal that are present at the first and second frequencies; and a processor configured to determine a characteristic of the sample based on the components of the science signal that are present at the first and second frequencies.

13. The system of claim 12, further comprising:

a coupler configured to combine the optical radiation from the first modulator and the second modulator into a combined signal.

14. The system of claim 13, further comprising:

an optical amplifier connected to the coupler and configured to amplify the combined signal and transmit the combined signal toward the sample.

15. The system of claim 12, further comprising:

a reference detector configured to detect the optical radiation from the first modulator and the second modulator before scattering/reflecting from the sample and generate a reference signal; and a second plurality of lock-in amplifiers respectively configured to generate components of the reference signal that are present at the first and second frequencies.

16. The system of claim 15, wherein the processor is further configured to determine the characteristic of the sample based on the components of the reference signal that are present at the first and second frequencies.

17. The system of claim 12, wherein the sweep frequency is lower than the first frequency and the second frequency.

18. The system of claim 12, wherein the reference wavelength lies outside the wavelength range.

19. A method of determining a concentration of material in a sample, comprising:

modulating wavelength-varying radiation at a first frequency;

modulating fixed-wavelength radiation at a second frequency;

detecting the wavelength-varying radiation and the fixed-wavelength radiation before scattering/reflecting from the sample to produce a local detection signal;

transmitting the wavelength-varying radiation and the fixed-wavelength radiation to the sample;

detecting the wavelength-varying radiation and the fixed-wavelength radiation after scattering/reflecting from the sample to produce a remote detection signal;

determining portions of the local detection signal and the remote detection signal at the first frequency;

determining portions of the local detection signal and the remote detection signal at the second frequency;

obtaining a transmission profile from the portions of the local detection signal and the remote detection signal at the first frequency and at the second frequency; and calculating the concentration of the material based on the transmission profile, wherein the first frequency is not harmonically related to and is different from the second frequency.

20. The method of claim 19, wherein the obtaining includes:

multiplying the portion of the remote detection signal at the first frequency by the portion of the local detection signal at the second frequency to obtain a first product, and dividing the first product by a second product of the portion of the local detection signal at the first frequency by the portion of the remote detection signal at the second frequency.

21. A system for remotely sensing a sample, comprising:

means for generating wavelength-varying radiation and fixed-wavelength radiation;

means for modulating the wavelength-varying radiation at a first frequency;

means for modulating the fixed-wavelength radiation at a second frequency; and means for detecting radiation at the first and second frequencies using a phase sensitive technique after the wavelength-varying radiation and the fixed-wavelength radiation have scattered/reflected from the sample, wherein the first frequency is not harmonically related to and is different from the second frequency.

22. The system of claim 21, further comprising:

means for detecting radiation at the first and second frequencies using a phase sensitive technique before the wavelength-varying radiation and the fixed-wavelength radiation have scattered/reflected from the sample.

* * * * *